US008100951B2

(12) United States Patent
Justis et al.

(10) Patent No.: US 8,100,951 B2
(45) Date of Patent: Jan. 24, 2012

(54) SURGICAL INSTRUMENTS AND TECHNIQUES FOR PERCUTANEOUS PLACEMENT OF SPINAL STABILIZATION ELEMENTS

(75) Inventors: Jeff R. Justis, Collierville, TN (US); John D Pond, Jr., Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 372 days.

(21) Appl. No.: 12/410,645

(22) Filed: Mar. 25, 2009

(65) Prior Publication Data
US 2009/0182382 A1 Jul. 16, 2009

Related U.S. Application Data

(62) Division of application No. 11/348,999, filed on Feb. 7, 2006, now Pat. No. 7,520,879.

(51) Int. Cl.
*A61B 17/88* (2006.01)
*A61B 17/70* (2006.01)

(52) U.S. Cl. ..................... 606/279; 606/86 A
(58) Field of Classification Search .......... 606/279, 606/86 A, 264–278
See application file for complete search history.

(56) References Cited

U.S. PATENT DOCUMENTS

| 4,448,191 | A | 5/1984 | Rodnyansky |
| 5,020,519 | A | 6/1991 | Hayes |
| 5,242,443 | A | 9/1993 | Kambin |
| 5,720,751 | A | 2/1998 | Jackson |
| 5,910,141 | A | 6/1999 | Morrison et al. |
| 6,183,472 | B1* | 2/2001 | Lutz .......................... 606/86 A |
| 6,226,548 | B1 | 5/2001 | Foley et al. |
| 6,235,028 | B1 | 5/2001 | Brumfield et al. |
| 6,485,491 | B1 | 11/2002 | Farris et al. |
| 6,530,929 | B1 | 3/2003 | Justis et al. |
| 6,648,888 | B1 | 11/2003 | Schluzas |
| 6,660,006 | B2 | 12/2003 | Markworth et al. |
| 6,740,089 | B2 | 5/2004 | Haider |
| 6,821,277 | B2 | 11/2004 | Telebaum et al. |
| 7,004,947 | B2 | 2/2006 | Shluzas et al. |
| 2002/0161368 | A1 | 10/2002 | Foley et al. |
| 2003/0199884 | A1 | 10/2003 | Davison et al. |
| 2003/0225408 | A1 | 12/2003 | Nichols et al. |
| 2004/0039384 | A1 | 2/2004 | Boehm, Jr. et al. |
| 2004/0049191 | A1 | 3/2004 | Markworth et al. |
| 2004/0138662 | A1 | 7/2004 | Landry et al. |
| 2004/0143265 | A1 | 7/2004 | Landry et al. |
| 2004/0172022 | A1 | 9/2004 | Landry et al. |
| 2004/0215190 | A1 | 10/2004 | Nguyen et al. |
| 2004/0267275 | A1 | 12/2004 | Cournoyer et al. |
| 2005/0010219 | A1 | 1/2005 | Dalton |

(Continued)

FOREIGN PATENT DOCUMENTS

DE 100 32 126 1/2002

(Continued)

*Primary Examiner* — Eduardo C Robert
*Assistant Examiner* — Ellen C Hammond

(57) ABSTRACT

Systems and methods for positioning a connecting element adjacent the spinal column in minimally invasive procedures include instruments that guide the connecting element from a location remote from one or more anchors to a location proximate to the one or more anchors. The instruments include extensions mountable to anchors, and inserter instruments mountable to the connecting element for positioning the connecting element adjacent the anchors in a minimally invasive procedure. The inserter instruments need not be mounted to the anchors or to the anchor extensions, and are operable independently thereof to position the connecting element into the patient along a minimally invasive insertion path from a location remote from the anchor extensions.

18 Claims, 13 Drawing Sheets

U.S. PATENT DOCUMENTS

| | | |
|---|---|---|
| 2005/0010221 A1 | 1/2005 | Dalton |
| 2005/0021031 A1* | 1/2005 | Foley et al. .................. 606/61 |
| 2005/0021040 A1 | 1/2005 | Beryagnoli |
| 2005/0033299 A1 | 2/2005 | Shluzas |
| 2005/0080418 A1 | 4/2005 | Simonson et al. |
| 2005/0085813 A1 | 4/2005 | Spitler et al. |
| 2005/0131408 A1 | 6/2005 | Sicvol et al. |
| 2005/0131421 A1 | 6/2005 | Anderson et al. |
| 2005/0131422 A1 | 6/2005 | Anderson et al. |
| 2005/0154389 A1 | 7/2005 | Sclover et al. |
| 2005/0171540 A1 | 8/2005 | Lim et al. |
| 2005/0182407 A1 | 8/2005 | Dalton |
| 2005/0192570 A1 | 9/2005 | Jackson |
| 2005/0192579 A1* | 9/2005 | Jackson .................. 606/72 |
| 2005/0192589 A1 | 9/2005 | Raymond et al. |
| 2005/0277934 A1* | 12/2005 | Vardiman .................. 606/61 |
| 2007/0078460 A1 | 4/2007 | Frigg et al. |

FOREIGN PATENT DOCUMENTS

| | | |
|---|---|---|
| WO | WO 01 28436 | 4/2001 |
| WO | WO 2007 025132 | 3/2007 |

* cited by examiner

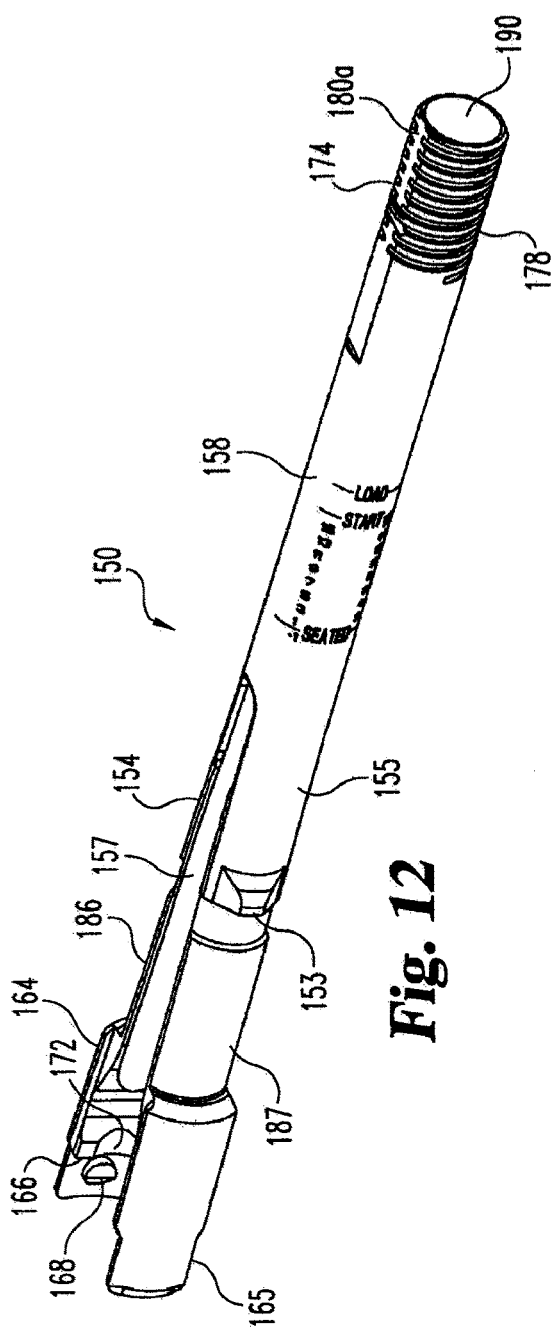
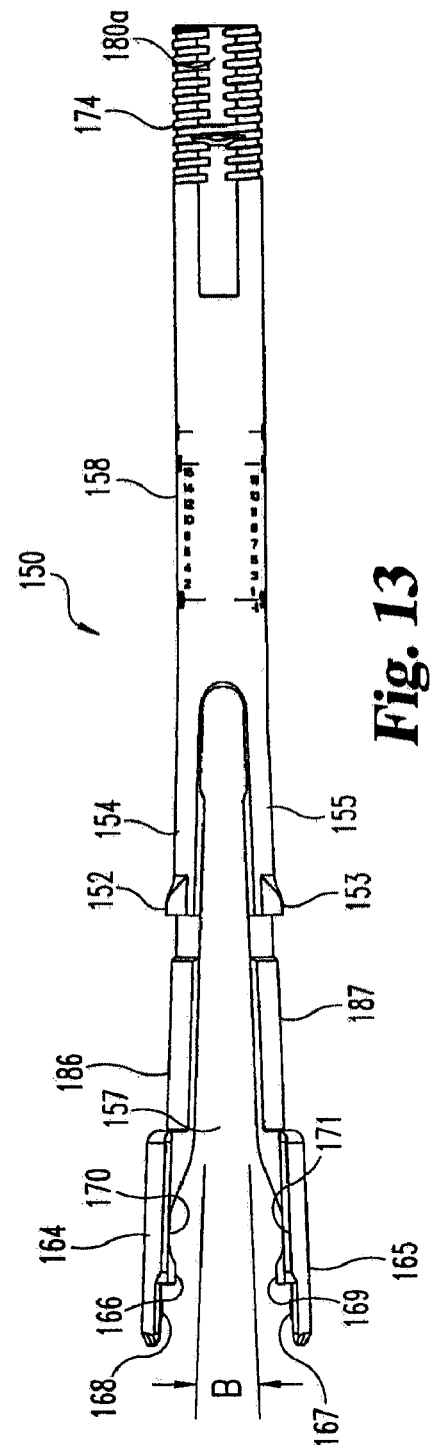

SURGICAL INSTRUMENTS AND TECHNIQUES FOR PERCUTANEOUS PLACEMENT OF SPINAL STABILIZATION ELEMENTS

This application is a divisional of U.S. application Ser. No. 11/348,999, filed Feb. 7, 2006, now U.S. Pat. 7,520,879, the entire contents of which are hereby incorporated by reference.

BACKGROUND

Various devices and methods for stabilizing bone structures have been used for many years. For example, the fracture of an elongated bone, such as a femur or humerus, can be stabilized by securing a plate to the fractured bone across the fracture. The plate extends across the fractured area and thus stabilizes the fractured components of the bones relative to one another in a desired position. When the fracture heals, the plate can be removed or left in place, depending on the type of plate that is used.

Another type of stabilization technique uses one or more elongated rods extending between components of a bony structure and secured to the bony structure to stabilize the components relative to one another. The components of the bony structure are exposed and one or more bone engaging fasteners are placed into each component. The elongated rod is then secured to the bone engaging fasteners in order to stabilize the components of the bony structure.

One problem associated with the above described stabilization structures is that the skin and tissue surrounding the surgical site must be cut, removed, and/or repositioned in order for the surgeon to access the location where the stabilization device is to be installed. This repositioning of tissue causes trauma, damage, and scarring to the tissue. There are also risks that the tissue will become infected and that a long recovery time will be required after surgery for the tissue to heal.

Minimally invasive surgical techniques are particularly desirable in, for example, spinal and neurosurgical applications because of the need for access to locations deep within the body and the presence of vital intervening tissues. The development of percutaneous minimally invasive spinal procedures has yielded a major improvement in reducing recovery time and post-operative pain because they require minimal, if any, muscle dissection and can be performed under local anesthesia. These benefits of minimally invasive techniques have also found application in surgeries for other locations in the body where it is desirable to minimize tissue disruption and trauma. There remains a need for further improvements instruments and methods for stabilizing bony structures using minimally invasive techniques.

SUMMARY

Systems and methods for positioning a connecting element adjacent the spinal column in minimally invasive surgical procedures include an inserter instrument and one or more anchor extensions removably engaged to one or more anchors engageable to the spinal column. The inserter instrument can be engaged to the connecting element and employed to insert the connecting element through tissue of the patient in a minimally invasive surgical procedure to a location adjacent to the one or more anchors with neither the connecting element nor the inserter instrument mechanically engaged with the extensions. Accordingly, the connecting element can be guided to a location proximate the anchors using freehand type techniques aided by image guided navigation, guidance structures, and/or tactile feel to provide cues to the surgeon during insertion. Once the connecting element is located adjacent the anchors, the extensions can be operable to seat the connecting element in the anchors for engagement of the connecting element to the anchors.

Related features, aspects, embodiments, objects and advantages of the present invention will be apparent from the following description.

BRIEF DESCRIPTION OF THE DRAWINGS

FIG. 12 is a perspective view of a first member of the extension of FIG. 8.

FIG. 13 is a side elevation view of the first member of FIG. 12.

DESCRIPTION OF THE ILLUSTRATED EMBODIMENTS

Figure 1:
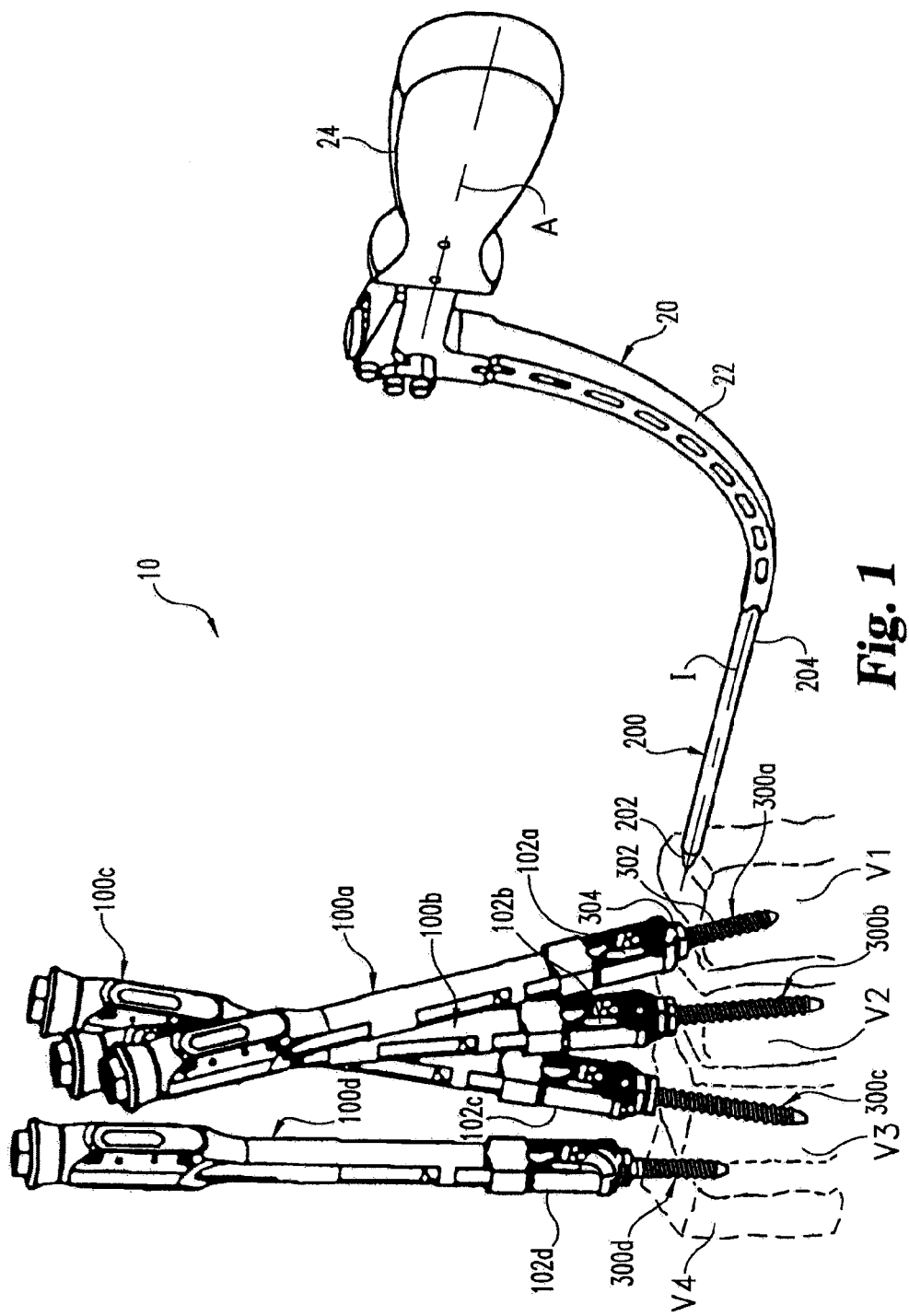
FIG. 1 is a perspective view of a system for positioning a connecting element in a patient in minimally invasive surgical procedures with the connecting element remotely positioned relative to the anchors and anchors extensions.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Systems and methods for insertion of a connecting element for connection with anchors engaged to bony parts of the body are provided. In one form, the systems include at least one anchor extension extending from at least one anchor engaged to the bony part of the body. An inserter instrument is engaged to the connecting element and is operable to position the connecting element through tissue of the patient from a location remotely positioned from the at least one anchor and anchor extension to a location adjacent to or within the anchor where the connecting element can be secured to the anchor. The anchor and connecting element can each be positioned into the patient in minimally invasive procedures, minimizing trauma and surgical risks to the patient and promoting rapid post-operative recovery. However, applications in non-minimally invasive surgeries are also contemplated.

In another form, the systems and methods include at least one extension extending from an anchor engaged to the spinal column or other anatomical structure in a patient. A connecting element is engaged to an inserter instrument, and the inserter instrument is movable without a mechanical association with the at least one extension to position the connecting element adjacent to a space defined by the extension adjacent to the anchor. The extension is operable to displace the connecting element in the space to seat the connecting element in the anchor for engagement to the anchor.

In a further form, the systems and methods include an inserter instrument engageable to a connecting element. The inserter instrument includes a handle portion at a proximal end thereof and the connecting element extends distally from the inserter instrument in a generally parallel relation to the handle portion.

In another form, the inserter instrument includes an inserter arm having a proximal handle portion extending therefrom in a first direction and a connecting element extending from a distal end thereof in a second direction opposite the first direction. The inserter arm can be curved between the handle portion and the distal end. The inserter instrument can also include a latch mechanism to releasably secure the connecting element to the distal end of the inserter arm.

In another form, the systems and methods include an inserter instrument having a handle portion, a curved inserter arm extending from the handle portion to a distal end, and an elongated, linear connecting element extending from the distal end of the inserter arm.

In a further form, the systems and methods include at least one anchor engageable to at least one vertebral body and an extension extending proximally from the at least one anchor to a proximal end of the extension. An inserter instrument includes a connecting element engaged thereto and is operable to position the connecting element through tissue to a location adjacent to the at least one anchor with neither the inserter nor the connecting element mechanically engaged or mechanically associated with the extension as the connecting element is positioned in the body of the patient.

In yet another form, the systems and methods include three or more anchors engageable to respective ones of three or more vertebral bodies and extensions extending proximally from respective ones of the anchors to a proximal end of the respective extension. An inserter instrument includes a connecting element engaged thereto and is operable to position the connecting element through tissue and serially between locations adjacent the at least three anchors with neither the inserter instrument nor the connecting element mechanically engaged or mechanically associated with any of the extensions as the connecting element is positioned in the body of the patient.

Figure 2:
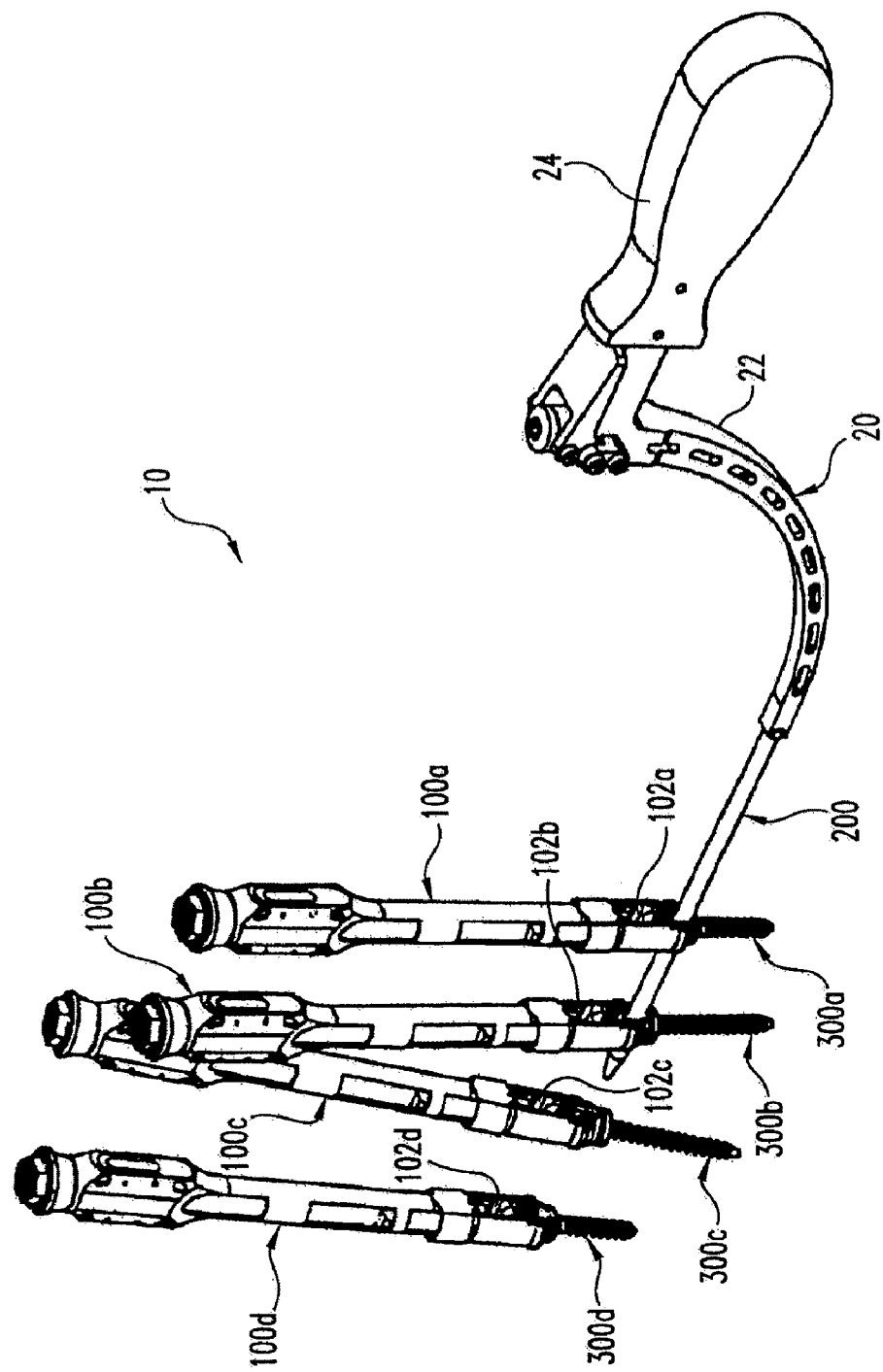
FIG. 2 is the system of FIG. 1 with the connecting element adjacent two of the anchors and anchor extensions of the system.
Figure 3:
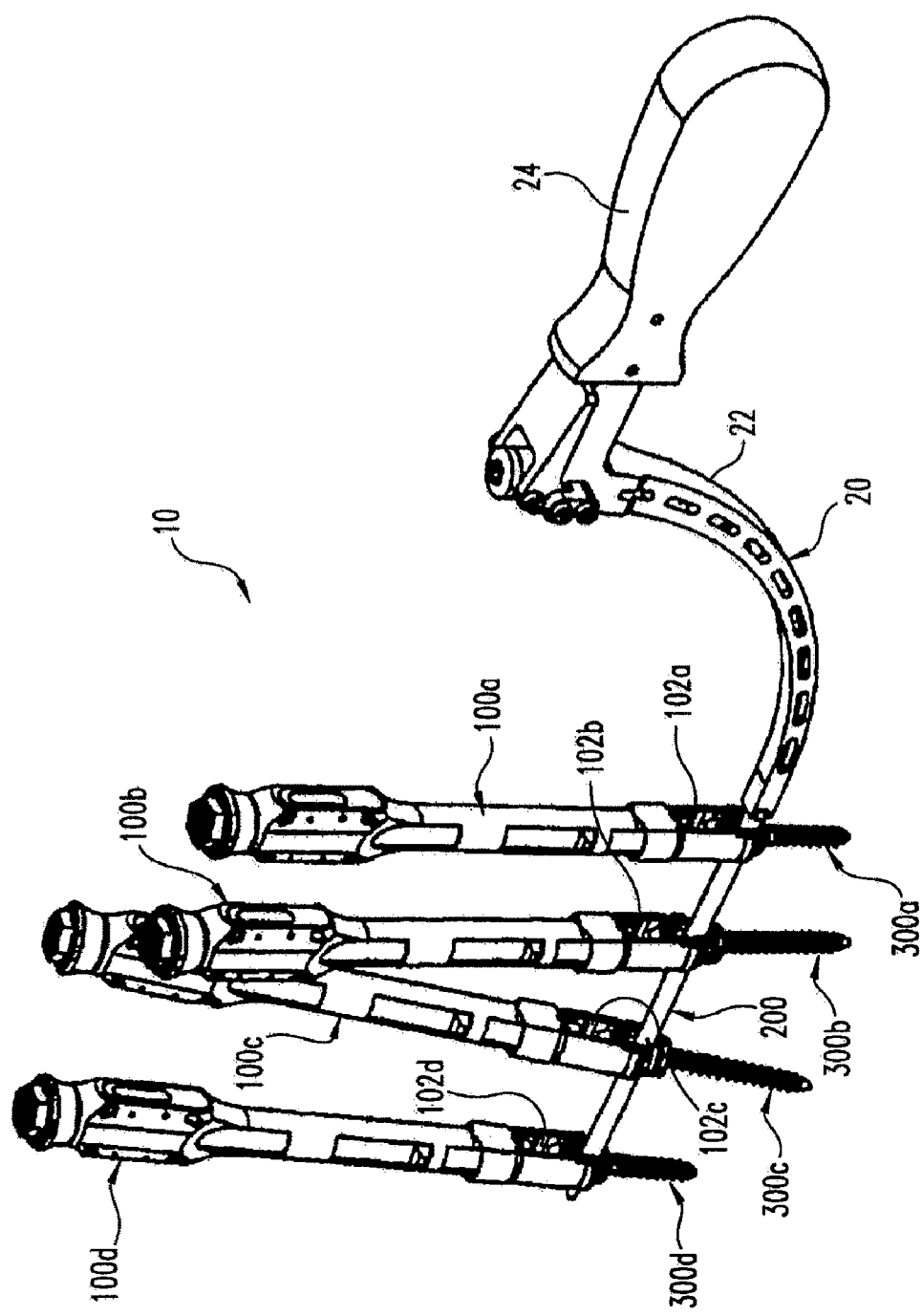
FIG. 3 is the system of FIG. 1 with the connecting element adjacent all the anchors and anchor extensions of the system.

Referring now to FIGS. 1-3, there is shown a minimally invasive surgical system 10 that includes an inserter instrument 20, four anchor extensions 100a, 100b, 100c, 100d (collectively and individually referred to herein as anchor extensions 100) and an elongated connecting element 200. Anchor extensions 100a, 100b, 100c, 100d are releasably mountable to respective ones of the anchors 300a, 300b, 300c, 300d (collectively and individually also referred to herein as anchors 300.) Anchors 300a, 300b, 300c, 300d are engaged to respective ones of the vertebrae V1, V2, V3, V4. Extensions 100 can include a length extending proximally from the respective anchors 300 so that at least the proximal ends thereof are located outside a respective wound or incision in the patient through which a respective one of the anchors 300 is positioned to engage the respective vertebra.

Inserter instrument 20 is movable along a percutaneous insertion path that starts at a location remote from the extensions 100 through skin and tissue of the patient to position connecting element 200 in a location adjacent the anchors 300. Inserter instrument 20 is operable to position the connecting element 200 with neither the connecting element 200 nor the inserter instrument 20 mechanically engaged or associated with any of the extensions 100 at least during the initial insertion.

Connecting element 200 can be an elongated brace, rod or shaft that is generally linear along its length to facilitate placement between three or more anchors. Other embodiments contemplate that connecting element 200 can be curved along all or a portion of its length. It is also contemplated that connecting element 200 can include any configuration known for a rod, implant, or fastener, so long as connecting element 200 is insertable using inserter instrument 20. Further, connecting element 200 can be non-rigid, elastic and/or super-elastic and in the form of a cable, band, wire, or artificial ligament that is used in tethering, guiding, or other surgical procedures. Connecting element 200 can be percutaneously or non-percutaneously inserted with inserter instrument 20 to a location adjacent connecting element engaging portions of one or more anchors engaged to a bony structure in the body of an animal subject to stabilize the bony structure.

In the illustrated embodiment, connecting element 200 is a rigid linear rod that forms an extension of inserter arm 22 of inserter instrument 20 along an axis I defined by connecting element 200. However, it is contemplated that connecting element 200 can have one or more offset portions or a curvature that varies or is compounded along its length. In the illustrated embodiment, inserter instrument 20 includes a handle portion at a proximal end of inserter arm 22 that extends along an axis A. In one embodiment, axis A is generally parallel to axis I and inserter arm 22 is curved between handle portion 24 and connecting element 200.

Connecting element 200 in FIG. 1 is inserted via the inserter instrument 20 to a location adjacent to anchors 300 where the connecting element 200 can be engaged to anchors 300 to stabilize the respective vertebrae V1, V2, V3 and V4. The inserter instrument 20 can be employed without mechanically engaging or associating the inserter instrument 20 or connecting element 200 with extensions 100 as the connecting element is placed through the skin and tissue of the patient. Insertion of connecting element 200 can be guided by fluoroscopic imaging techniques, tactile feel and indications, and/or other suitable arrangements. Examples of imaging techniques are disclosed in U.S. Pat. No. 6,226,548, for example, which is incorporated herein by reference in its entirety.

In FIG. 1 the leading end 202 of connecting element 200 is shown in an approach to anchor 300a with trailing end 204 of connecting element 200 engaged to a distal end of inserter arm 22. Extension 100a forms a space 102a adjacent anchor 300a for receiving connecting element 200. By grasping handle portion 24, the surgeon can manipulate leading end 202 and connecting element 200 through the tissue of the patient and through space 102a toward space 102b formed between extension 100b and anchor 300b for placement therethrough, as shown in FIG. 2. Serial advancement of connecting element 200 through spaces 102c and 102d formed between extensions 100c and 100d and the respective anchors 300c, 300d can continue as shown in FIG. 3. When connecting element 200 is positioned between the desired number of anchors, connecting element 200 can be engaged to the anchors with a suitable engaging member, such as a set screw, nut or other engaging member. In a further embodiment, connecting element 200 is seated relative to the anchors by operation of one or more of the extensions 100 before engaging connecting element 200 to anchors 300. Such seating can take the form of a spinal reduction procedure where one or more vertebrae are pulled or moved into alignment, and then engaged and maintained in this alignment by engagement of connecting element 200 thereto via the anchors 300.

In one embodiment, one or more of the extensions 100a, 100b, 100c, 100d can include a first member for engaging the respective anchor 300 and a second member movable relative to the first member engaged to the anchor to reduce or seat the connecting element for engagement with one or more of the anchors 300. After connecting element 200 is placed in the respective space 102 between the anchor and its respective extension, the one or more anchor extensions 100 with reduction capability can be manipulated so that the second member and the anchor 300 move relative to one another to seat the connecting element 200 relative to the anchor. Engaging members can be delivered through the respective extensions to engage the connecting element 200 to the respective anchors 300.

Anchors 300 include a bone engaging portion 302 and a connecting element engaging portion 304. In the illustrated embodiment, bone engaging portion 302 is a bone screw with a threaded shank to engage the bony structure of the underlying vertebra. Connecting element engaging portion 304 can be a receiver having a U-shape formed by a pair of opposing arms defining a longitudinal passage alignable along insertion axis I. The arms further define a proximal/distally extending opening that opens at a proximal end of the arms to receive a set screw (not shown) to secure connecting element 200 in the passage with connecting element 200 extending from the respective anchor 300 along insertion axis I. Bone engaging portion 302 can be pivotally received in or coupled to connecting element engaging portion 304 through a distal opening thereof, and structured to interact therewith to provide anchor 300 with multi-axial capabilities that permits either a selected number of positions or an infinite number of positions of bone engaging portion 302 relative to connecting element engaging portion 304.

Other forms for anchors 300 are contemplated, including uni-axial and uni-planar bone screws. The bone engaging portion 302 can be in the form of a spike, staple, fusion device, cannulated screw, fenestrated screw, interbody device, intrabody device, clamp, plate, suture anchor, bolt, pin or other bone engaging member. The connecting element engaging portion 304 can be in the form of a saddle, yoke, eye-bolt or through-hole, side opening member, bottom opening member, top-opening member, eyelet, or any other structure engageable to the connecting element.

Figure 4:
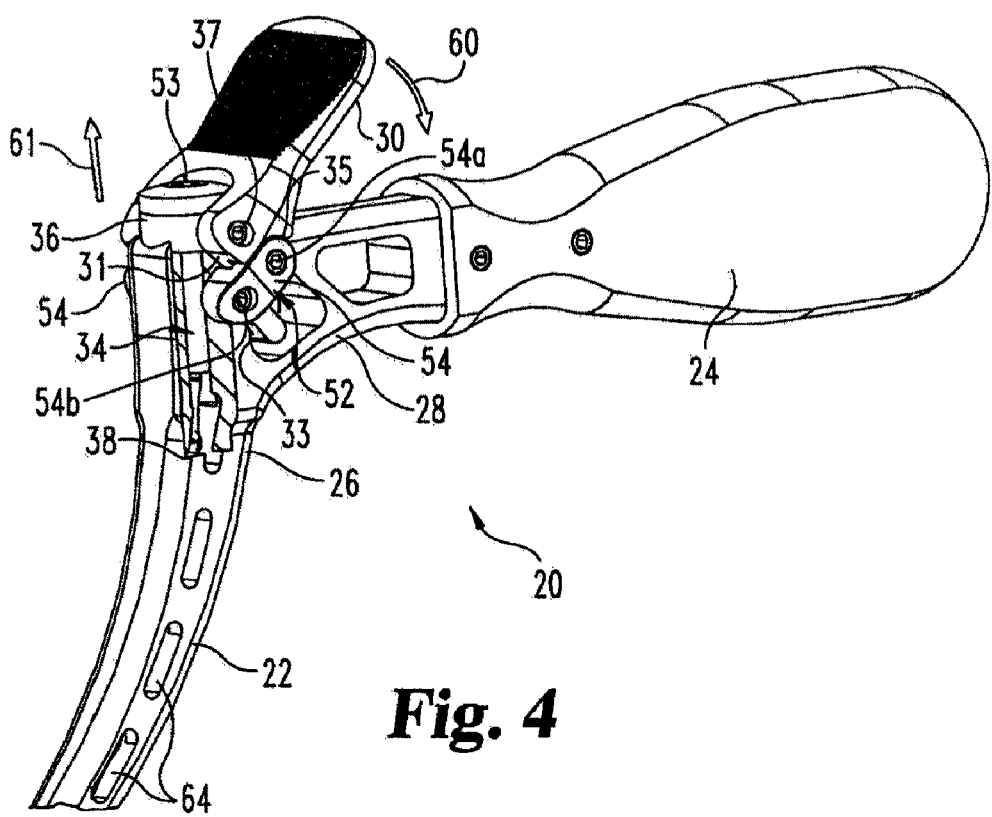
FIG. 4 is a perspective view in partial section of a proximal portion of an inserter instrument with a latch mechanism in an open position.
Figure 5:
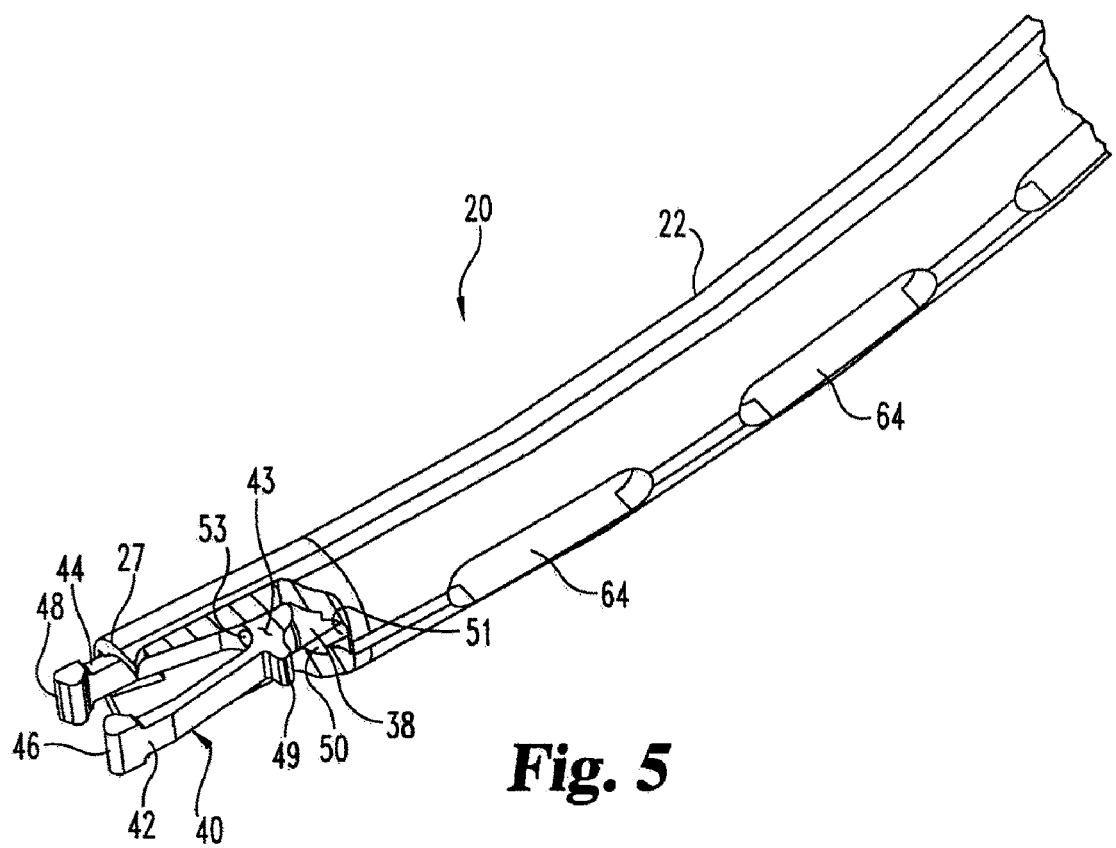
FIG. 5 is a perspective view in partial section of a distal portion of the FIG. 4 inserter instrument when the latch mechanism is in an open position.

Referring now further to FIGS. 4-7, there is shown further details of inserter instrument 20. In FIGS. 4-5, inserter instrument 20 is in an open position to receive or release connecting element 200, and in FIGS. 6-7 inserter instrument 20 is in a closed or locked position for engaging the connecting element 200 to inserter arm 22. Inserter instrument 20 includes handle portion 24 extending from a proximal end 26 of inserter arm 22. Inserter arm 22 extends transversely to handle portion 24 and its proximal portion forms generally an "L" shape with handle portion 24 adjacent a proximal end 26 of inserter arm 22. Handle portion 24 can be sized and shaped to receive the palm of a user's handle and smoothly contoured to facilitate manual control of inserter instrument 20.

Inserter arm 22 and handle portion 24 come together at a junction portion 28 formed by a frame of inserter instrument 20. Inserter arm 24 can be tapered in cross-sectional size from proximal end 26 to a narrower distal end 27. Junction portion 28 includes an actuating member 30 pivotally coupled at an upper or proximal side of the frame at junction portion 28 for easy access by the user of inserter instrument 20. Actuating member 30 is coupled to and operates a locking mechanism 34 that extends through inserter arm 22 to remotely secure and release the connecting element 200 to the distal end of inserter arm 22. Actuating member 30 extends from its pivotal connection with the frame at junction 28 toward handle portion 24, and can have an open position shown in FIG. 4 where actuating member 30 extends upwardly from handle portion 24, and can be pivoted relative to handle portion 24 and inserter arm 22 to the closed or locked position shown in FIG. 6 where actuating member 30 extends along the portion of the frame extending between inserter arm 22 and handle portion 24.

Locking mechanism 34 is coupled with actuating member 30 so that movement of actuating member 30 in turn translates into movement of locking mechanism 34, Locking mechanism 34, in the illustrated embodiment, includes a proximal end cap 36 (FIGS. 4 and 6) protruding or located proximally of inserter arm 22, and a shaft portion 38 extending distally from end cap 36 through bore 50 of inserter arm 22 to a distal engaging end 40 (FIGS. 5 and 7) opposite end cap 36. Actuating member 30 is pivotally coupled with end cap 36 at a pivot end 37.

Actuating member 30 is further pivotally coupled with inserter 20 at junction 28 with a coupling mechanism 52. Specifically, actuating member 30 provides an over-center type lever or latch that is operable to displace locking mechanism 34 distally and proximally in inserter arm 22. Actuating mechanism 30 includes opposite ears 31 pivotally coupled with one end 54a of respective link members 54 of coupling mechanism 52. A cross member 33 extends between ears 31 through an opening of the frame at junction portion 28. The other end 54b of link members 54 are each pivotally coupled with inserter arm 22 adjacent proximal end 26. Accordingly, when actuating member 30 is moved as indicated by arrow 60, end cap 36 and locking mechanism 34 are displaced proximally as indicated by arrow 61 from the position in FIG. 4 to the position shown in FIG. 6.

Figure 6:
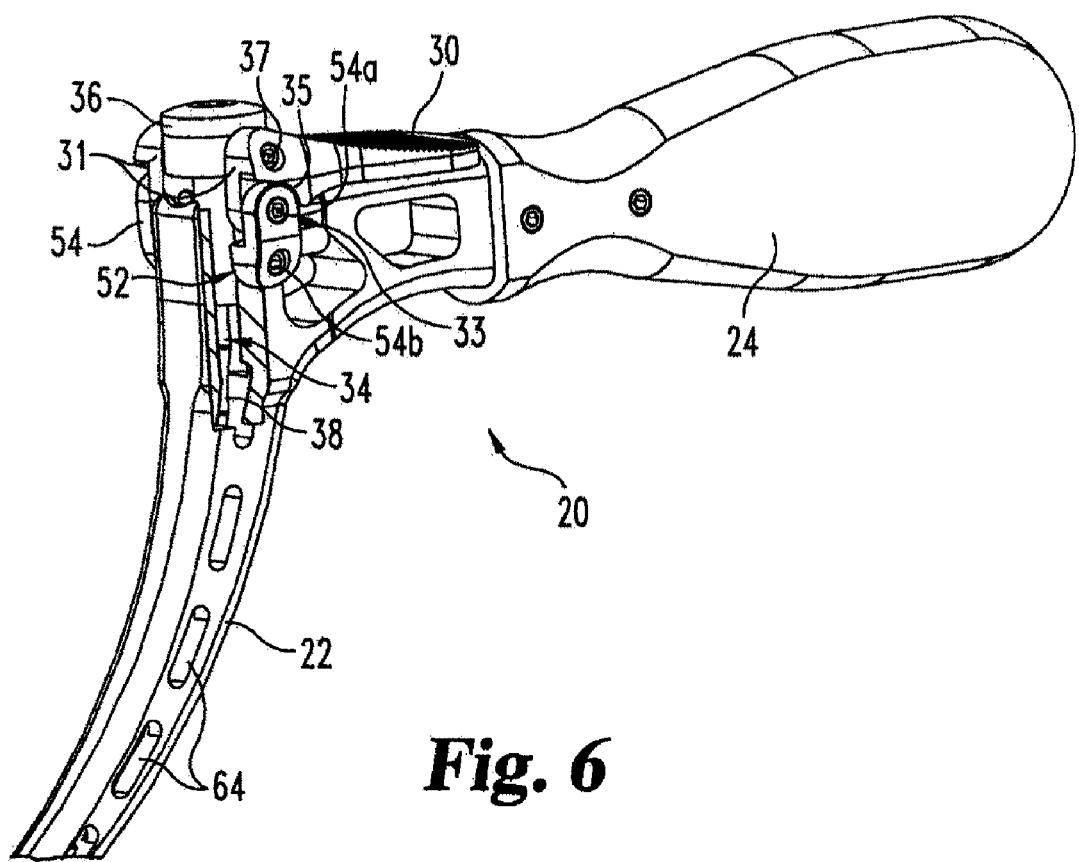
FIG. 6 is a perspective view in partial section of the proximal portion of the inserter instrument of FIG. 4 with the latch mechanism in a closed position.

In the closed position, link members 54 are generally orthogonally oriented to actuating member 30, as shown in FIG. 6. Contact between a convex end of link member 54 and a concave surface 35 along actuating member 30 can maintain actuating member 30 in the closed position until sufficient force is applied in the direction opposite arrow 60 to pivot link member 54 and actuating member 30 about their respective pivotal coupling locations to the orientations shown in FIG. 4.

Figure 7A:
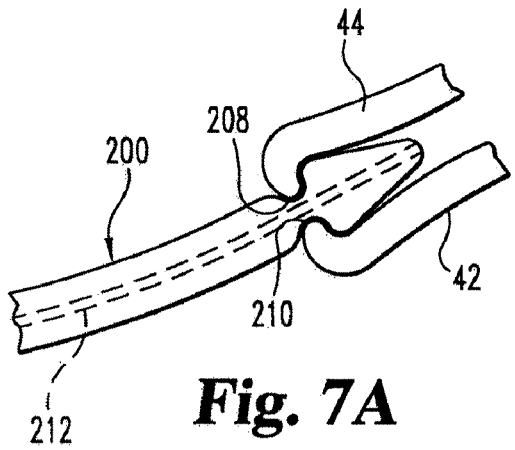
FIG. 7A is a view showing engagement of the locking mechanism of the inserter instrument with the connecting element.
Figure 7:
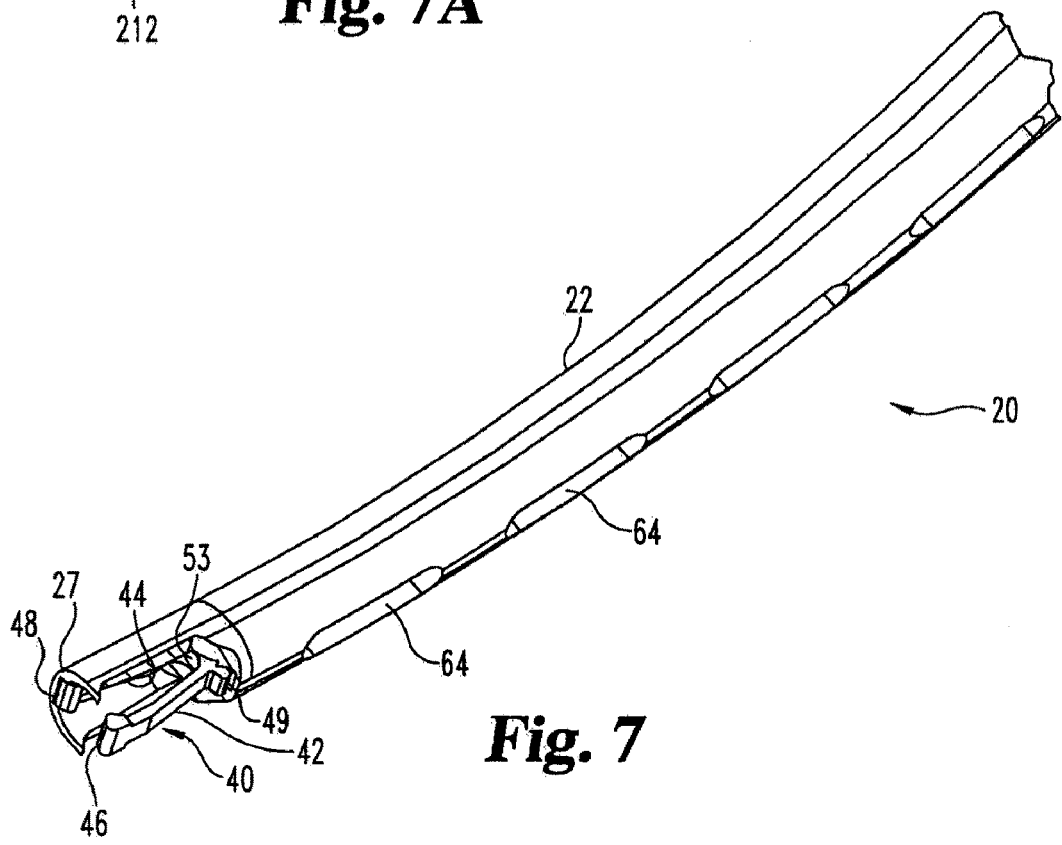
FIG. 7 is a perspective view in partial section of the distal portion of the inserter instrument of FIG. 4 when the latch mechanism is in a closed position.

As shown in FIGS. 5 and 7, engaging end 40 of locking mechanism 34 includes a first arm 42 and a second arm 44 coupled to one another about an integral or living hinge 43. Each of the arms 42, 44 includes a distal end member 46, 48, respectively, that project from distal end 27 of inserter arm 22 when actuating member 30 is in the open position of FIG. 5. In this position, arms 42, 44 can move relative to one another by flexing about hinge 43 and permit insertion of trailing end 204 of connecting element 200 therebetween. Actuating member 30 is moved to the closed position to displace shaft portion 38 in bore 50 and retract arms 42, 44 into bore 50 and into contact with the inner wall surface adjacent distal end 27 of inserter arm 22 as shown in FIG. 7. A projection 49 extending from arm 42 can be received in a slot 51 along bore 50 to maintain locking mechanism 34 in alignment as it is moved along bore 50 into and out of inserter arm 22. Distal end members 46, 48 are maintained in respective receptacles 208, 210 of connecting element 200, as shown in FIG. 7A, to securely engage connecting element 200 to inserter instrument 20.

Other configurations for engaging end 40 are also contemplated. For example, engaging end 40 can be provided as a collet with bifurcated wall portions or other radially expandable and contractable structure to grippingly engage connecting element 200 thereto. In a further form, locking mechanism 34 can include a lumen 53 extending along and opening between arms 42, 44 and at the end of end cap 36 to receive a guide wire or other guiding structure. Connecting element 200 can further be provided with a lumen 212 therethrough that forms an axial extension of lumen 53, permitting connecting element 200 and inserter instrument 20 to be guided percutaneously over a guide wire while engaged to one another. Sidewall holes 64 in inserter arm 22 are in communication with the central bore 50 thereof, further facilitating cleaning and sterilization and removal of any biomaterial that may be trapped therein.

Referring now to FIGS. 8-11, one embodiment of the anchor extensions 100 is shown engaged to an anchor 300. Anchor extension 100 includes a first member in the form of an inner sleeve positioned within outer sleeve 101. Anchor extension 100 also includes a second member in the form of an outer sleeve 101 extending along an elongated body 104. Space 102 is formed distally of outer sleeve 101 between flanged ends 164, 165 of inner sleeve 150.

With respect to outer sleeve 101, elongate body 104 includes elongated intermediate slots 108a, 108b extending and opening along opposite sides thereof. Slots 108a, 108b extend between a proximal end 109 and a distal end 110. Body 104 includes a distal end portion 105 that forms a wall that extends completely therearound in form fitting and sliding engagement with flanged ends 164, 165. Body 104 includes a length extending from distal end portion 105 to an enlarged proximal end portion 112. Proximal end portion 112 includes opposite flat wall surfaces 114a, 114b and a release button 116 pivotally housed in proximal end portion 112 in each of the wall surfaces 114a, 114b (only one button 116 shown.) Opposite wall surfaces 118a, 118b of proximal end portion 112 extend between flat wall surfaces 114a, 114b.

Proximal end portion 112 further includes an end collar 120 having a reducing actuator 122 rotatably captured thereto. In the illustrated embodiment, reducing actuator 122 includes a bearing hub 124 that extends between reducing actuator 122 and an inner wall surface of end collar 120 to rotatably and axially retain reducing actuator 122 on outer sleeve 101. Accordingly, reducing actuator 122 can be rotated relative to outer sleeve 101 while being axially retained in position thereon. Reducing actuator 122 can extend proximally from end collar 120 for easy access and manipulation during the surgery. Reducing actuator 122 can be rotated manually, or can be configured to engage a tool. For example, in the illustrated embodiment reducing actuator 122 is configured like a nut to receive a correspondingly shaped tool to facilitate application of rotational forces. Other embodiments contemplate other arrangements suitable for manual grasping and/or grasping by a tool.

Figure 11:
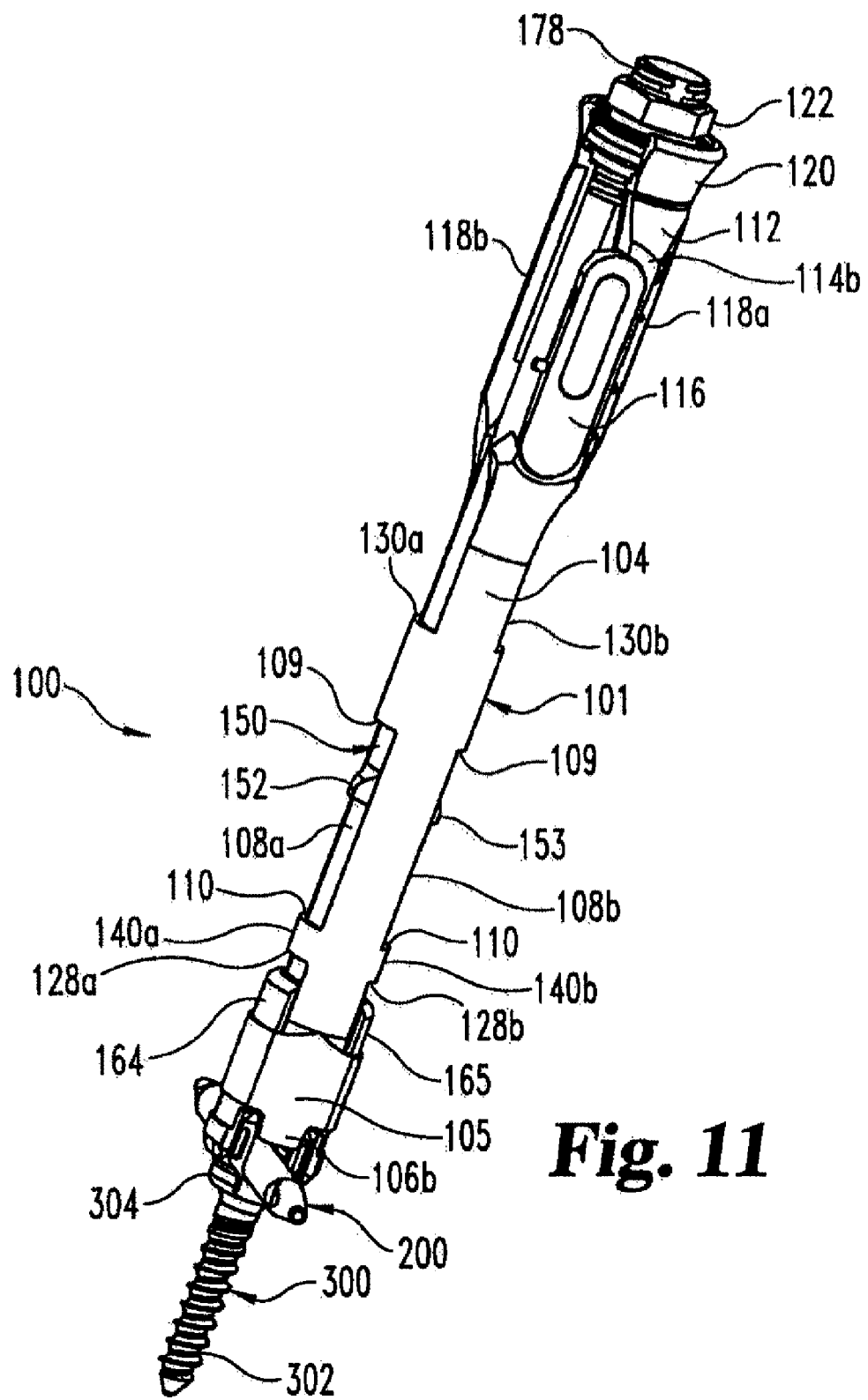
FIG. 11 is a perspective view of the extension of FIG. 8 in partial section and manipulated to a seating configuration to seat a connecting element in the anchor.

Distal end portion 105 includes distal projecting members 106a, 106b extending therefrom on opposite sides of body 104 and between the flanged ends 164, 165 of inner sleeve 150. Body 104 further defines distal slots 128a, 128b aligned with respective ones of the intermediate slots 108a, 108b and extending therefrom toward the distal end portion 105. Flanged ends 164, 165 extend through distal slots 128a, 128b as inner sleeve 150 is moved proximally relative outer sleeve 101, as shown in FIG. 11. Wall portions 140a, 140b extend between respective ones of the slots 108a, 128a and slots 108b, 128b. Body 104 also defines proximal slots 130a, 130b aligned with respective ones of the slots 108a, 108b and extending proximally therefrom toward the proximal end portion 112.

Anchor extension 100 further includes inner sleeve 150 positioned in a bore extending Through outer sleeve 101. Inner sleeve 150, shown removed from outer sleeve 101 in FIGS. 12-13, includes a tubular body 158 defining distal fingers 154, 155. Fingers 154, 155 are separated by a slot 157 to facilitate fingers 154, 155 moving toward and away from another to capture anchor 300 therebetween. In their normal position, fingers 154, 155 are flared distally away from one another in non-parallel relation by an angle B both to receive anchor 300 therebetween and when engaged to anchor 300. Fingers 154, 155 include distal flanged ends 164, 165, respectively, that project outwardly for axial sliding engagement with distal end portion 105 of outer sleeve 101.

Figure 14:
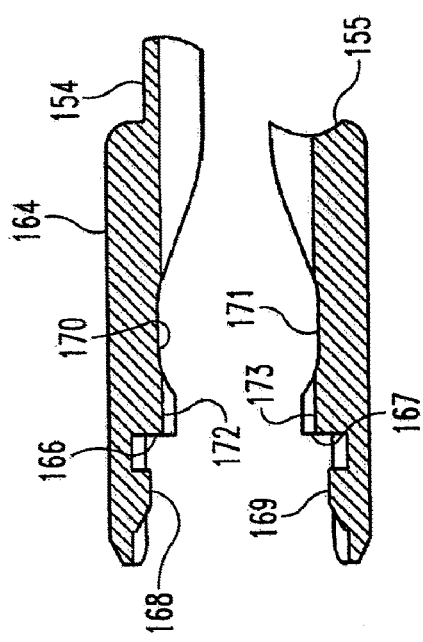
FIG. 14 is a longitudinal section view of a distal portion of the first member of FIG. 12.

As also shown in FIG. 14, flanged ends 164, 165 further each include an internal lip 166, 167 that abuttingly engages an adjacent proximal end of the anchor 300 received therein. The internal lips 166, 167 can each include a longitudinally extending concave surface, such as surfaces 172, 173, respectively, that extend along the passage defined between fingers 154, 155 to facilitate placement of a set screw or other engaging member thereby and into the anchor 300 engaged between fingers 154, 155. Flanged ends 164, 165 each further include a projection or nub 166, 167 distally of the respective lips 166, 167 that engage an adjacent recess or detent in anchor 300 when 30 flanged ends 164, 165 are clamped to the connecting element engaging portion 304.

Flanged ends 164, 165 each further include a concavely curved inner wall portions 170, 171 that form an enlarged space between fingers 154, 155 extending in a direction that is transversely oriented to fingers 154, 155. Inner wall portions 170, 171 are spaced proximally from internal lips 166, 167 in order to be located proximally of connecting element engaging portion 304 of the anchor 300 when flanged ends 164, 165 are clamped thereto. This enlarged space defined by wall portions 170, 171 can be employed to allow passage of a connecting element through space 102 between fingers 154, 155 even if the connecting element has an enlarged or non-uniform cross-section along a portion of its length. Examples of such connecting elements are discussed in U.S. Patent Application Publication No. 2005/0171540, which is incorporated herein by reference in its entirety.

Fingers 154, 155 also each include a projecting member 152, 153, respectively, extending therefrom through respective ones of the slots 108a, 108b of outer sleeve 101. Projecting members 152, 153 can maintain the inner and outer sleeves 101, 150 in alignment with one another as they are axially moved relative to one other and to resist rotation of inner sleeve 150 relative to outer sleeve 101. As outer sleeve 101 is advanced distally along fingers 154, 155, distal end portion 105 extending about fingers 154, 155 contacts the outer surfaces of flanged ends 164, 165 and biases flanged ends 164, 165 into engagement with anchor 300. The outer surfaces of fingers 154, 155 can project outwardly along intermediate portions 186, 187 between flanged ends 164, 165 and projecting members 152, 153 to provide a larger cross-section adjacent flanged ends 164, 165. When wall portions 140a, 140b of outer sleeve 101 are moved from their FIG. 8 positioning to their positioning in FIGS. 9 and 10, wall portions 140a, 140b can contact intermediate portions 186, 187 to facilitate positive closure of the flanged ends 164, 165 against anchor 300.

Figure 15:
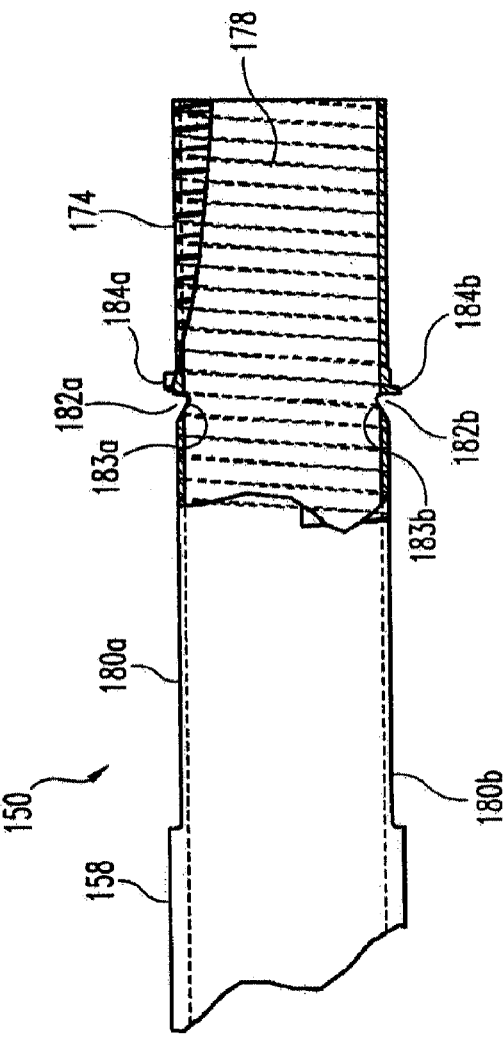
FIG. 15 is an elevation view in partial section of a proximal end portion of the first member of FIG. 12.

As also shown in FIG. 15, the proximal end portion 174 of body 158 includes an externally threaded section 178 for engagement by reducing actuator 122. Accordingly, rotation of reducing actuator 122 along threaded section 178 causes axial displacement of inner and outer sleeves 101, 150 relative to one another. Threaded section 178 further includes an outer wall surface having opposing, non-threaded flats 180a, 180b extending therealong and also distally therefrom along a portion of the length of body 158. A recess 182a, 182b is formed in each of the flats 180a, 180b, and a protrusion 184a, 184b extends outwardly from the respective flats 180a, 180b adjacent to and proximally of the respective recess 182a, 182b.

Figure 8:
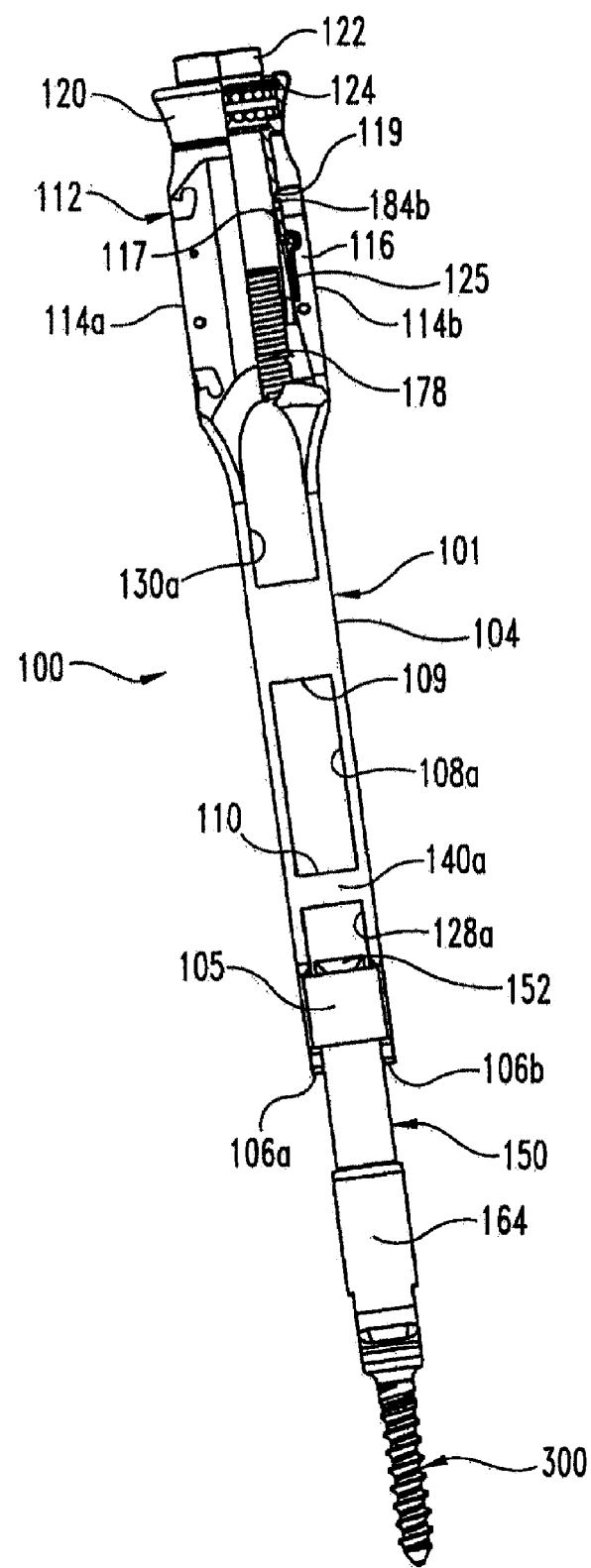
FIG. 8 is an elevation view of an extension in partial section and in a loading configuration where it is in removable engagement to an anchor.
Figure 9:
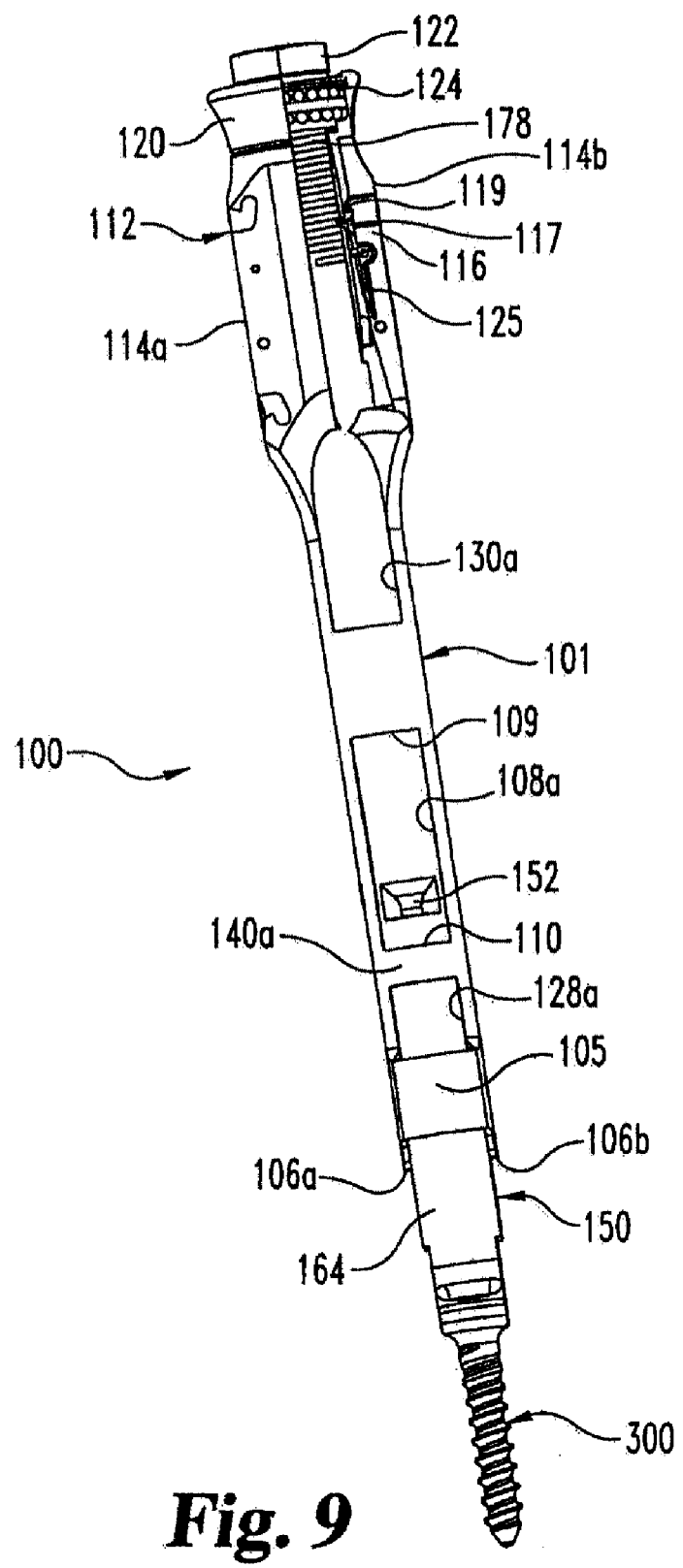
FIG. 9 is an elevation view of the extension of FIG. 8 in a starting configuration where it is securely engaged to the anchor.

Buttons 116 can be elongated and extend axially along extension 100. Each button 116 can include a proximal end with a first distal projection 117 and a second proximal projection 119, as shown in FIGS. 8 and 9. A spring member 125 can bias button 116 about its pivotal connection 121 with outer sleeve 101 so that projections 117, 119 are normally pivoted toward inner sleeve 150. In the starting configuration of FIGS. 9-10, distal projection 117 is received in the respective adjacent recess 182a, 182b and the proximal projection 119 is positioned proximally of the respective adjacent protrusion 184a, 184b. In this configuration, the contact between projection 119 and the respective protrusion 184a, 184b prevents proximal movement of inner sleeve 150 relative to outer sleeve 101, and the contact between distal projection 117 and the respective recess 182a, 182b prevents inner sleeve 150 from moving distally relative to outer sleeve 101.

Buttons 116 can be depressed and rotated against the bias of spring 125 about connection 121 so that the projections 117, 119 cannot interfere with inner sleeve 150, and inner sleeve 150 can be displaced distally relative to outer sleeve 101 to a loading configuration, as shown in Fig. 8. In this configuration, arms 154, 155 can be flexed apart and so that flanged ends 164, 165 can be positioned on opposing sides of the respective anchor 300. To firmly clamp flanged ends 164, 165 to the anchor 300, inner sleeve 150 is displaced proximally relative to outer sleeve 101 to the starting configuration shown in FIGS. 9-10. In this configuration, distal end portion 105 contacts the outer surfaces of flanged ends 164, 165 to prevent arms 154, 155 from moving apart and tightly grips flanged ends 164, 165 to the anchor 300.

From the starting configuration, inner sleeve 150 can be moved proximally relative to outer sleeve 101 so that distal projecting members 106a, 106b contact connecting element 200 extending in space 102 transversely to flanged ends 164, 165. Advancement of connecting element 200 into contact with projecting members 106a, 106b is accomplished by rotating reducing actuator 122 about threaded end section 178 of inner sleeve 150, as shown in FIG. 11, until connecting element 200 is firmly seated in the connecting element engaging portion 304 of anchor 300. A set screw or other engaging member can be delivered through passage 190 of inner sleeve 150 and engaged to connecting element engaging portion 304 to engage and maintain connecting element 200 therein.

To permit proximal displacement of inner sleeve 150 from its starting configuration without depressing button 116, recesses 182a, 182 include distally sloped wall portions 183a, 183b, as shown in FIG. 15, that contact correspondingly shaped distally sloped wall portions of the respective adjacent distal projection 117. As inner sleeve 150 is initially moved proximally relative to outer sleeve 101 from the starting configuration of FIGS. 9-10, the sloped wall portions slide along one another to pivot button 116 about its connection 121 and move the proximal end of button 116, and thus proximal projection 119, away from inner sleeve 150 so that proximal projection 119 cannot contact the respective protrusion 184a, 184b extending from inner sleeve 150. Projection 117 can slide along the respective adjacent non-threaded flat wall surface 180a, 180b as inner sleeve 150 is advanced further proximally relative to outer sleeve 101.

Figure 10:
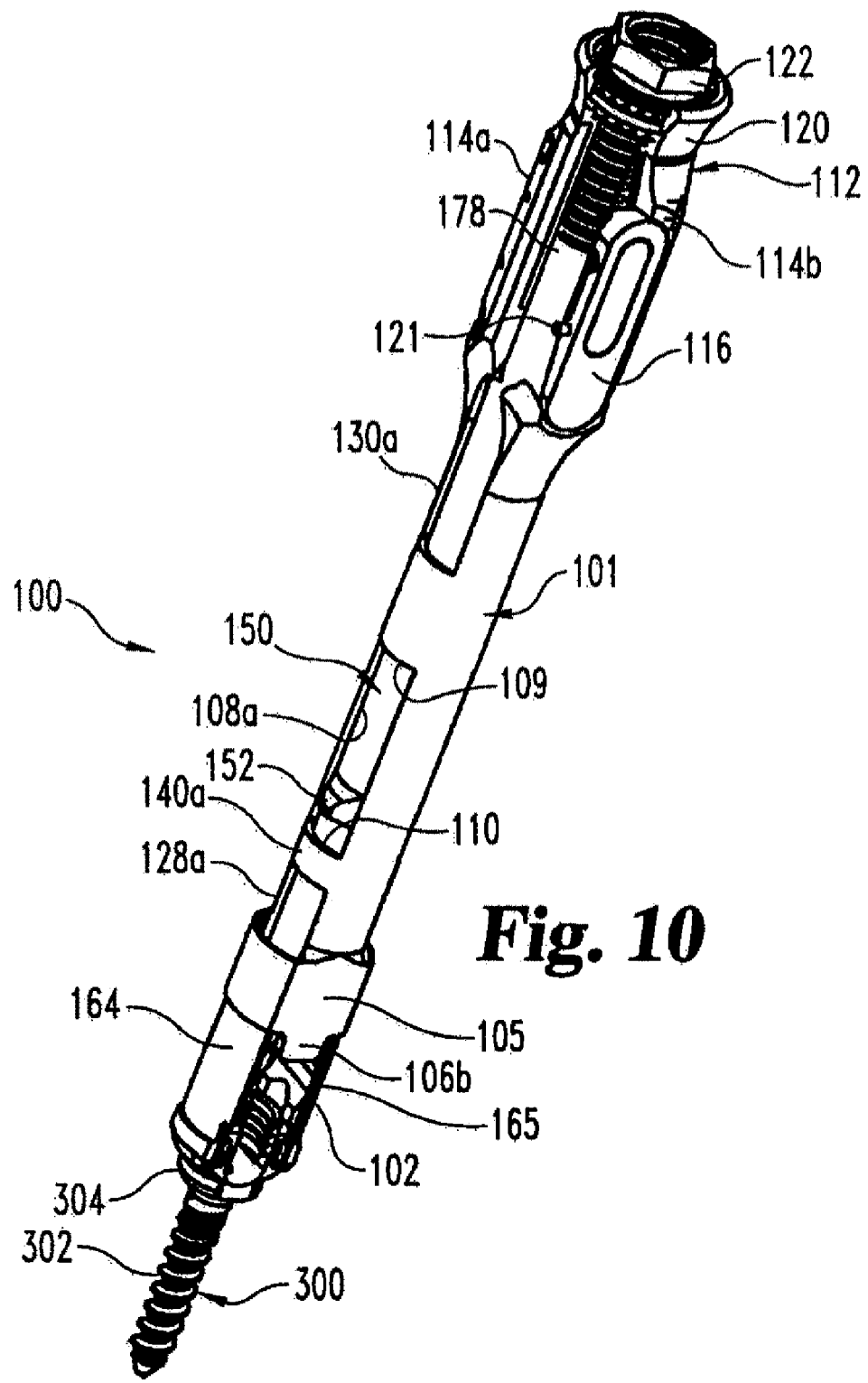
FIG. 10 is a perspective view of the extension and anchor of FIG. 9.

Inner sleeve 150 can include calibrations or other indicators on its outer surface to provide an indication of the configuration of the inner sleeve relative to the outer sleeve. Such indicators can be provided on inner sleeve 150 and visualized through one or both of the proximal slots 130a, 130b of outer sleeve 101 to provide visual cues of the configuration of extension 100. For example, one indicator can indicate that the extension 100 is in the loading configuration for engaging anchor 300 to arms 154, 155, as shown in FIG. 8. Another indicator can indicate that the extension is in the starting configuration as shown in FIGS. 9 and 10. In the starting configuration, anchor 300 is securely engaged between flanged ends 164, 165 but outer sleeve 101 is positioned proximally of anchor 300 to form space 102 to receive connecting element 200 between flanged ends 164, 165 proximal of the anchor. Space 102 can be elongated to provide a location adjacent to anchors 300, in addition to the connecting element engaging portions 304, in which the connecting element 200 can be initially positioned relative to the anchors 300, and connecting element 200 need not be guided directly into the connecting element engaging portion 304. A third indicator can indicate that connecting element 200 is seated in anchor 300 since inner sleeve 150 is displaced proximally relative to outer sleeve 101 to force connecting element 200 into the connecting element engaging portion 304 of anchor 300.

In order to uncouple extension 100 from anchor 300 after seating and securing connecting element 200 in anchor 300, reducing actuator 122 is rotated in the opposite direction to proximally displace outer sleeve 101 along inner sleeve 150 until extension 100 is in its starting configuration. With reducing actuator 122 not engaged to threaded section 178, buttons 116 can then be pressed to disengage inner sleeve 150 and allow outer sleeve 101 to slide freely proximally relative to inner sleeve 150 to the loading configuration of FIG. 8. Arms 154, 155 can then flex outwardly away from one another as the extension 100 is pulled off of anchor 300 to disengage anchor 300 from between flanged ends 164, 165.

Various surgical techniques can be completed with system 10. One type of surgical technique is directed to spinal surgery for positioning an elongated connecting element along one or more vertebral levels to provide spinal stabilization. A number of anchors 300 are selected according to the number of vertebral levels to be instrumented. For example, a single level procedure may include an anchor engaged to each of two vertebrae, or a two level procedure may include an anchor engaged to each of three vertebrae.

When the desired number of levels has been selected, anchors 300 can be engaged to the respective vertebrae. In posterior spinal surgical techniques, the anchors 300 can be screws engaged in the pedicles of the vertebrae. Anchors 300 can be positioned into the patient through one or more minimally invasive access portals, formed by an incision, cannula, or retractor system, for example. Extensions 100 can be clamped to the anchors after the anchors are engaged to the vertebrae. Alternatively, the anchors can be clamped to the extensions, and then delivered through the access portal or portals for engagement with the respective vertebrae. Placement of the anchors can be facilitated using a guide wire, image guided surgery system, fluoroscopic imaging, computer assisted surgical navigation, X-rays, CT scans, endoscopic viewing systems, microscopic viewing systems, loupes, and/or naked eye visualization, for example.

With the anchors 300 engaged to the vertebrae and with extensions 100 extending therefrom, extensions 100 have a length sufficient to extend from the patient so that their proximal ends are accessible for grasping and pivoting or application of forces to facilitate alignment of the connecting element engaging portions 304 of the anchors 300. For example, distraction, compression or torsional forces can be provided to one or more of the extensions 100 to provide a desired effect to the vertebrae either before of after placement of the connecting element between the anchors.

The connecting element 200 can enter the patient percutaneously or through a retracted opening from an entry location remote from the extensions. The connecting element is guided by the surgeon through the tissue to a location adjacent the nearest anchor 300 and anchor extension 100 and into the space 102 defined thereby. The connecting element can then be serially advanced through the other spaces 102 defined by the other anchors 300 and extensions 100. Placement of the connecting element 200 can be facilitated using a guide wire, image guided surgery system, fluoroscopic imaging, computer assisted surgical navigation, X-rays, CT scans, endoscopic viewing systems, microscopic viewing systems, loupes, and/or naked eye visualization, for example. One or more sensors can be provided in or on the connecting element 200 to assist in tracking its location in the patient. For example, a magnetic tracking coil could be mounted on a wire and placed in a cannulation of the connecting element near its distal leading end. Electromagnetic surgical navigation of placement of the connecting element into the patient's body can then be carried out. In addition, tactile cues can be provided to the surgeon assist placement in the space between the extension and anchor if and when the connecting element contacts the anchor or extension.

Prior to placement of connecting element 200, a trocar can be engaged to inserter instrument 20 and moved into the patient from a location outside the patient, through skin and/or tissue of the patient, and to at least one of the anchors 300. Inserter instrument 20 can be withdrawn in the reverse direction to withdraw the trocar. The trocar can then be removed from inserter instrument 20, and connecting element 200 engaged to inserter instrument 20 to move it along the insertion path formed in the patient by the trocar until the connecting element extends between anchors 300. It is further contemplated that the leading end of connecting element 200 can be tapered or pointed to facilitate puncture and/or tunneling through the skin and tissue of the patient, either to form a path or to be inserted along a path formed by a trocar. Placement of the trocar and/or connecting element 200 can be monitored and/or confirmed using any of the visualization techniques discussed above.

Connecting element 200 can be remotely disengaged from inserter instrument 20 by manipulating actuating member 30 to release engaging end 40 of locking mechanism 34 from connecting element 200. Inserter instrument 20 can then be withdrawn from the patient by pulling it with handle portion 24 in the reverse direction along the insertion path. Set screws or other engaging members can be delivered through extensions 100 with a driving instrument, and engaged with respective ones of the anchors 300 to secure connecting element 200 to anchors 300. Extensions 100 can then be unclamped from the respective anchors 300 by depressing buttons 116 and allowing the outer sleeve to slide proximally relative to inner sleeve, releasing arms from engagement with connecting element engaging portion 34 of anchor 300. Should any of the extensions 100 be employed for reduction of the connecting element into the anchors, the corresponding extensions are first moved from the seating configuration to the starting configuration before unlocking with buttons 116.

One or more other connecting elements can be similarly engaged to the spinal column along the same vertebral level or levels, or along other vertebral levels. Other procedures can also be completed in conjunction with the stabilization procedure, including discectomy, interbody fusion, artificial disc replacement, bore removal, tissue removal, intravertebral reduction, joint replacement, annular repair, and/or any other spinal surgical procedures.

While the invention has been illustrated and described in detail in the drawings and foregoing description, the same is to be considered as illustrative and not restrictive in character, it being understood that all changes and modifications that come within the spirit of the invention are desired to be protected.

What is claimed is:
1. A method for stabilizing a portion of a spinal column, comprising:
engaging at least one anchor to at least one vertebra;
providing an extension from the at least one anchor with the extension extending proximally from the at least one anchor to a proximal end remote from the at least one anchor; and
guiding a connecting element through tissue of a patient to a space adjacent the anchor with an inserter instrument including a proximal handle portion and an inserter arm extending distally from said proximal handle portion, wherein said inserter arm includes a curved profile from said handle portion to a distal end of said inserter arm, wherein said inserter arm includes a bore with a locking mechanism therein, said locking mechanism including a shaft portion extending between an engaging end adjacent a distal end of said inserter arm and an opposite end coupled to an actuating member adjacent a proximal end of said inserter arm, wherein said shaft portion extends along said curved profile of said inserter arm from said engaging end to said opposite end, said actuating member being pivotally mounted to said inserter instrument for movement between an unlocked position wherein said engaging end projects from said distal end of said inserter arm to receive said connecting element to a locked position wherein said actuating member moves said engaging end into said bore of said inserter arm, said inserter arm engaging said engaging end as said engaging end is moved therein to engage said connecting element to said engaging end; and wherein neither the connecting element nor the inserter instrument are engaged to or guided by the extension to the space.

2. The method of claim 1, further comprising:
engaging a trailing end of the connecting element to an end of the inserter instrument with the connecting element extending from the inserter to a leading end of the connecting element spaced from the inserter instrument.

3. The method of claim 2, wherein the leading end of the connecting element is tapered.

4. The method of claim 2, wherein engaging the trailing end of the connecting element includes actuating a locking mechanism of the inserter instrument to secure an engaging end of the locking mechanism about the trailing end of the connecting element.

5. The method of claim 2, wherein engaging the trailing end of the connecting element includes engaging the connecting element in a generally parallel relation with a proximal handle portion of the inserter instrument.

6. The method of claim 5, wherein the inserter instrument includes an inserter arm that is curved between the proximal handle portion and the connecting element.

7. The method of claim 1, wherein the at least one anchor includes three or more anchors each of which includes an extension extending proximally from the anchor to a respective proximal end of the extension.

8. The method of claim 7, wherein guiding the connecting element includes serially advancing the connecting element adjacent to a receiver of a first one of the anchors and then adjacent to a second receiver of a second one of the anchors and then adjacent to a third receiver of a third anchor so that the connecting element extends between the receivers of the anchors.

9. The method of claim 8, further comprising manipulating the extensions to seat the connecting element into the receivers of the respective anchors.

10. The method of claim 9, further comprising engaging the connecting element seated in each of the receivers to the receiver of the respective anchor.

11. The method of claim 9, wherein the extensions each include a first member with a pair of arms clamped to opposite sides of the respective anchor, the pair of arms forming a space therebetween for receiving the connecting element, the extension each further including a second member proximal of the space, and manipulating the extensions includes distally advancing the second member into contact with the connecting element.

12. A method for stabilizing a portion of a spinal column, comprising:
engaging at least one anchor to at least one vertebra;
providing an extension from each of the at least one anchors with the extension extending proximally from the respective anchor to a proximal end remote from the at least one anchor, wherein the extension includes a first member having a distal portion engaged to the anchor forming a space adjacent to the respective anchor and a second member proximal of the space;
engaging a connecting element with a distal end of an inserter arm of an inserter instrument, the inserter instrument including a proximal handle portion extending from a proximal end of the inserter arm, wherein said inserter arm includes a curved profile from said handle portion to a distal end of said inserter arm,
guiding the connecting element through tissue of a patient to the space formed by each of the anchor extensions with the proximal handle portion of the inserter instrument; and
advancing the second member of each of the extensions into contact with the connecting element to seat the connecting element into each anchor;
wherein said inserter arm includes a bore with a locking mechanism therein, said locking mechanism including a shaft portion extending between an engaging end adjacent a distal end of said inserter arm and an opposite end coupled to an actuating member adjacent a proximal end of said inserter arm, wherein said shaft portion extends along said curved profile of said inserter arm from said engaging end to said opposite end, said actuating member being pivotally mounted to said inserter instrument for movement between an unlocked position wherein said engaging send projects from said distal end of said inserter arm to receive said connecting element to a locked position wherein said actuating member moves said engaging end into said bore of said inserter arm, said inserter arm engaging said engaging end as said engaging end is moved therein to engage said connecting element to said engaging end.

13. The method of claim 12, wherein the handle portion extends generally parallel to the connecting element when the connecting element is engaged to the distal end of the inserter arm.

14. The method of claim 12, wherein neither the inserter instrument nor the connecting element are engaged to either of the extensions while guiding the connecting element through tissue at least until the connecting element is in the space formed by at least one of the anchor extensions.

15. The method of claim 14, wherein advancing the second member of each of the extensions includes rotating a reducing actuator relative to the second member and about a threaded section of the first member to proximally displace the first member relative to the second member.

16. The method of claim 15, wherein the distal portion of the first member includes a pair of arms and a sleeve portion extending proximally from the pair of arms and the second member includes an outer sleeve positioned about the first member and movable relative thereto to force the pair of arms into clamping engagement with the respective anchor.

17. The method of claim 16, wherein the pair of arms of the first member include flanged ends extending therealong adjacent a distal end thereof for securely clampingly engaging the anchor therebetween when a distal end portion of the outer sleeve is positioned about the flanged ends.

18. The method of claim 16, wherein a distal end of the outer sleeve includes opposite, distally extending projecting members located between the pair of arms of the first member on respective sides of the pair of arms for contacting the connecting element when advancing the second member.

* * * * *